United States Patent [19]

Woods

[11] Patent Number: 4,615,701

[45] Date of Patent: Oct. 7, 1986

[54] INTRAOCULAR LENS AND METHOD OF IMPLANTATION THEREOF

[76] Inventor: Randall L. Woods, Rte. 4, Box 65, Clinton, Mo. 64735

[21] Appl. No.: 670,044

[22] Filed: Nov. 13, 1984

Related U.S. Application Data

[63] Continuation-in-part of Ser. No. 567,641, Jan. 3, 1984.

[51] Int. Cl.$^4$ ............................................. A61F 2/16
[52] U.S. Cl. ..................................................... 623/6
[58] Field of Search ............................ 3/13, 1; 623/6

[56] References Cited

U.S. PATENT DOCUMENTS

| | | | |
|---|---|---|---|
| 4,092,743 | 6/1978 | Kelman | 623/6 |
| 4,199,566 | 7/1979 | Shearing | 623/6 |
| 4,251,887 | 2/1981 | Anis | 623/6 |
| 4,261,065 | 4/1981 | Tennant | 623/6 |
| 4,298,994 | 11/1981 | Clayman | 623/6 |
| 4,363,143 | 12/1982 | Callahan | 3/13 |
| 4,370,760 | 2/1983 | Kelman | 623/6 |
| 4,494,254 | 1/1985 | Lopez | 3/13 |
| 4,527,294 | 7/1985 | Heslin | 3/13 |

OTHER PUBLICATIONS

Lens Styles from Cilco (advertisement brochure) 6 pages, pp. 1,2,4 and 6 cited, Styles SAC 3, SAC 5, PC 15, S2 and S2-B, Cilco, Inc. 1616 13th Ave., Box 1680, Huntington, West VA, Oct. 1982.

Intraocular Lens Implantation-Techniques & Complications (Book) by Clayman et al, the C. V. Mosby Co. (publisher) 1983, pp. 152-155.

*Primary Examiner*—Ronald L. Frinks
*Attorney, Agent, or Firm*—Schmidt, Johnson, Hovey & Williams

[57] ABSTRACT

An intraocular lens for use following extracapsular cataract extraction is provided with an optic that has one or more resilient haptics secured at the inner end thereof to the optic and normally extending outwardly from the optic, terminating in a free outermost end spaced from the peripheral edge of the optic. Prior to lens implantation the elongated haptic is placed under tension until its outer end is adjacent the optic, forming a loop, and the outer end is adjacent the optic, forming a loop, and the outer end of the haptic is then releasably attached to the optic, maintaining the tension and the loop. After implantation of the lens the outer end of the haptic is detached from the optic and, by virtue of the memory retaining characteristic thereof, the position fixation haptic returns toward its normal position extending outwardly from the optic, eliminating the loop.

15 Claims, 20 Drawing Figures

INTRAOCULAR LENS AND METHOD OF IMPLANTATION THEREOF

This application is a continuation-in-part of my co-pending application Ser. No. 06/567,641 filed Jan. 3, 1984 with the same title as the instant application.

Implantation of intraocular lenses in the human eye by ophthalmic surgeons following cataract extraction by extracapsular surgery has become increasingly popular among opthalmologists generally and quite gratifying to their patients, resulting in the advent of multitudes of lens suggestions, especially in regard to types of position fixation haptics that are secured to the optic of the lens. The lens implant, placed in the eye to improve vision, is normally located either in front of the pupil, within the pupil or behind the pupil. When placed behind the pupil, the lens may be positioned either inside or in front of the lens capsule. After the lens is in position behind the pupil it can be stabilized either within the ciliary sulcus or within the lens capsule or bag.

During extracapsular cataract surgery, the lens capsule is incised and the cataractal lens material is removed by suction, usually accompanied by irrigation. Hence, placement of the artificial lens behind the pupil and within the capsule bag is much more difficult than placement in the ciliary sulcus because the lens must be passed through the relatively small pupillary and capsular openings without tearing or otherwise traumatizing the intraocular structures, i.e., the iris and the lens capsule.

The difficulty arises from the fact that present day intraocular lenses are much too large for easy passage through the pupillary or capsular openings and no suggestion has heretofore been made for reducing the dimensions of the lenses prior to and during implantation. For example, the overall length of most presently available intraocular lenses is approximately 14 millimeters whereas the eye opening through which the lens must pass for implantation in the capsule is normally no longer than about 6 to 7 millimeters.

According to my invention, therefore, there is provided an intraocular lens which may be reduced in size prior to implantation, permitting placement behind the pupil either within the ciliary sulcus or, more particularly, within the capsule bag because of its capability of easily passing through the pupillary opening and/or capsular without any traumatizing effects on either the iris or the lens capsule.

My improved posterior chamber, intraocular lens is provided with one or more flexible strands or haptics that may be positioned close to the lens optic for ease or implantation into the capsular bag or ciliary sulcus and then released to move to the peripheral limits of the lens capsule or ciliary sulcus for centration and fixation of the intraocular lens.

The instant invention relates to means for holding the haptic(s) in a closed position during implantation together with means permitting release thereof for movement to its normal, expanded position after implantation. The haptic is releasably locked relatively close to the peripheral edge of the optic, forming a loop. Upon release of the haptic after the lens is in the eye the haptic springs back away from the edge of the optic by virtue of the memory retention characteristic of the resilient haptic.

When closed, the lens will pass easily through the pupil and even through the opening in the capsule. Openings are provided in the optic for receiving the normally free ends of the haptics, and such ends are specially formed to hold them in place before and during implantation.

Figure 1:
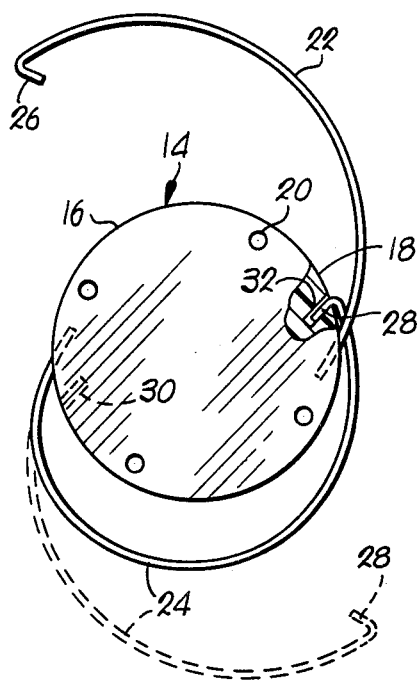
FIG. 1 is an elevational view of one form of intraocular lens made in accordance with my invention and adaptable for use in my novel method of implantation thereof.
Figure 2:
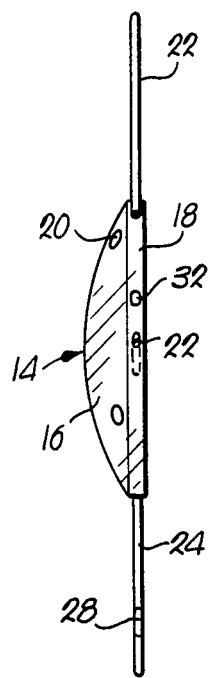
FIG. 2 is an edge view thereof.
Figure 7:
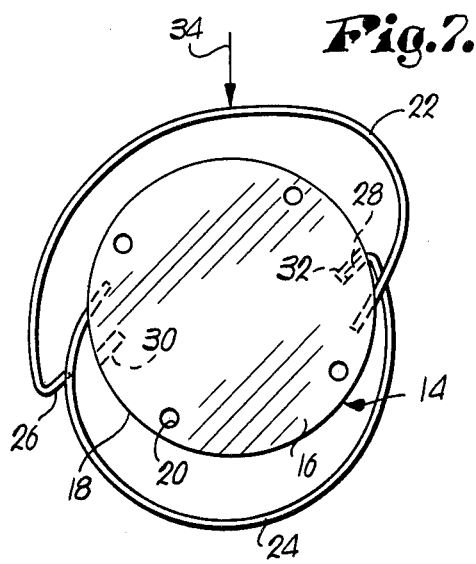
FIG. 7 is a view similar to FIG. 1 showing one way of releasing one of the haptics after implantation.

In FIGS. 1, 2 and 7 of the drawings there is shown an intraocular lens 14 adapted to be implanted in the human eye by the extracapsular surgeon and provided with an optic 16 having peripheral edge 18 which may be circular as shown, or otherwise, the optic 16 chosen for illustration of the concepts of the instant invention being plano-convex, having a predetermined size as well as the required dioptric, provided with the usual positioning holes 20 and made from any suitable material such as clear or tinted polypropylene, polymethylmethacrylate or their equivalents.

The optic 16 may be provided with one or more elongated, positioning haptics, two such haptics 22 and 24 being illustrated. Each is characterized by its resilient, memory retaining properties and may be made from the same materials as the optic 16. The arcuate, normally semi-circular haptics 22, 24 have their innermost ends secured to the optic 16 in diametrically opposed relationship, and each extends outwardly from the edge 18 in tangential relationship thereto.

The haptic 22 terminates at its outermost, free end in a hook 26 normally spaced radially outwardly from the edge 18 as shown by full lines FIG. 1. Similarly, the haptic 24 has a hook 28 at its outermost, free end normally spaced from the edge 18 as illustrated in dotted lines. The entire lengths of the haptics 22, 24 may be coplanar with the edge 18 as shown in FIG. 2 or at an angle to the edge 18. The optic 16 has a pair of diametrically opposed, hook-retaining openings 30 and 32 extending chordlike into the edge 18, the opening 30 being adapted to receive the hook 26 and the hook 28 being shown by full lines within the opening 32 both in FIG. 1 and in FIG. 7.

Prior to implantation of the lens 14 into a human eye the yieldable haptics 22, 24 are placed under tension and the hooks 26, 28 inserted into the openings 30 and 32 in locked relationship to the optic 16. They remain in such tensioned condition during implantation until the optic 16 and both haptics 22 and 24 are inside the eye. Noteworthy are the loops formed in haptics 22 and 24 when so tensioned (as shown in FIGS. 1 and 7 in the haptic 24) thereby reducing the maximum diameter of the lens 14 from loop to loop, obviating the difficulty of implantation.

After the lens 14 has been properly positioned in the eye such position is fixed by release of the hooks 26, 28 from within the opening 30, 32, such release being accomplished through use of a suitable instrument (hook, forceps or the like) to press the bights of the haptic loops inwardly toward the edge 18 as shown then return toward their normal positions and configurations with their outermost ends spaced from the edge 18.

Figure 3:
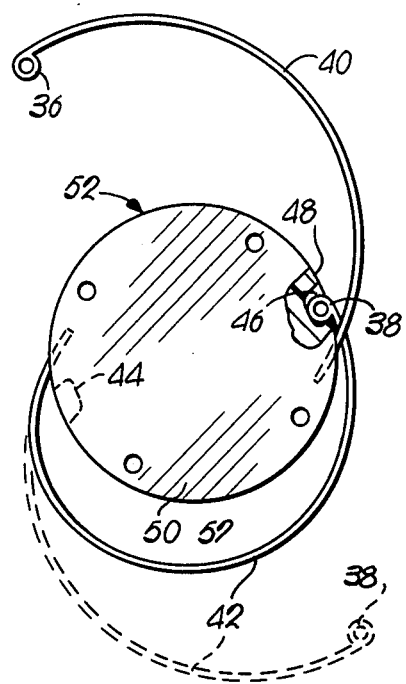
FIG. 3 is an elevational view of a first modified form of lens.

In FIG. 3 of the drawings, eyelets 36 and 38, adapted for receiving hook-like instruments, are provided on the outermost ends of haptics 40 and 42. These perforated nodules 36, 38 are adapted for releasable hooking into openings 44 and 46 within peripheral edge 48 of optic 50 of lens 52. Otherwise, the lens 52 and the method of implantation thereof are the same as above explained with respect to the lens 14.

Figure 4:
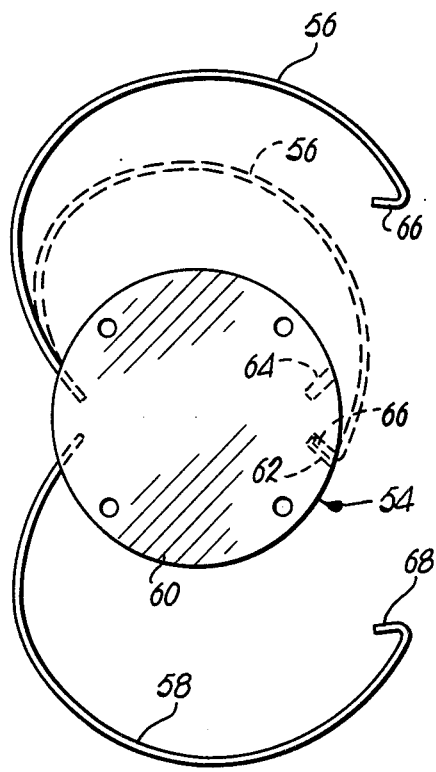
FIG. 4 is an elevational view of a second modified form of lens.

Whereas the haptics 22 and 24 for the lens 14 and the haptics 40 and 42 for the lens 52 extend from the edges 18 and 48 in the same directions, circumferentially of the optics 16 and 50, a lens 54 is shown in FIG. 4 with a pair of haptics 56 and 58 which extend circumferentially in opposite directions from the peripheral edge of optic 60.

The inner ends of haptics 56, 58 are spaced but a short distance from each other and, likewise, openings 62 and 64 for hooks 66 and 68 are but slightly spaced in diametrically opposed relation to the inner, fixed ends of the haptics 56, 58.

Figure 6:
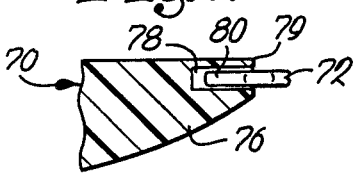
FIG. 6 is an enlarged, fragmentary, detailed, cross-sectional view taken on line 6—6 of FIG. 5.
Figure 5:
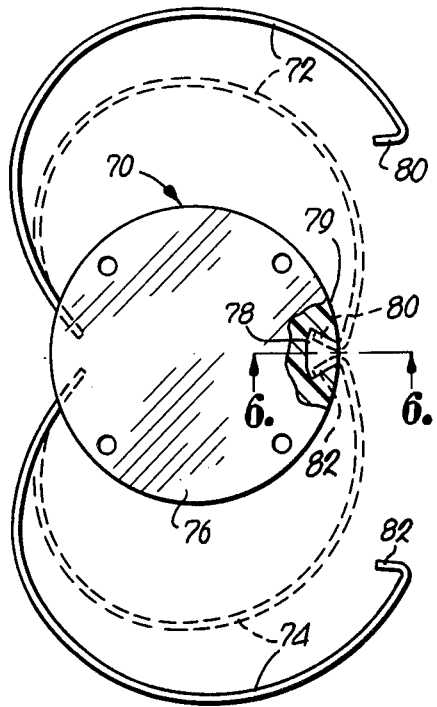
FIG. 5 is an elevational view of a third modified form of lens.

A lens 70, shown in FIGS. 5 and 6, has a pair of haptics 72 and 74 secured to an optic 76 in the same manner as in FIG. 4, but an opening 78 is provided in peripheral edge 79 of the optic 76 which is common to hooks 80 and 82 on the outer ends of the haptics 72 and 74.

Figure 8:
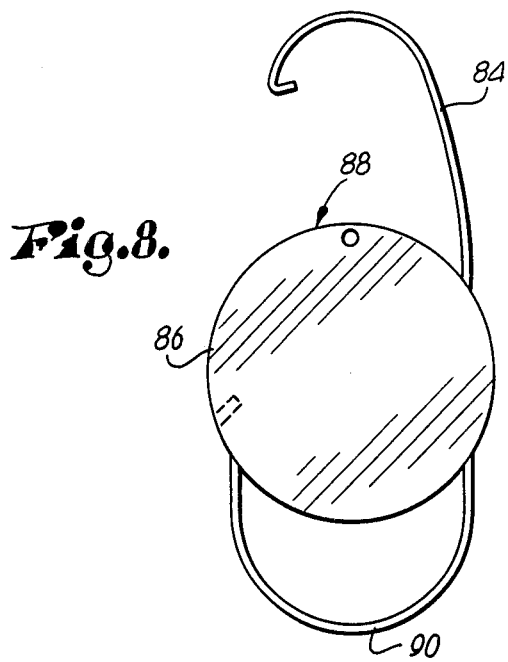
FIG. 8 is an elevational view of a fourth modified form of lens.

FIG. 8 of the drawings illustrates the way in which a single, J-shaped haptic 84 of the kind shown in FIGS. 1, 2 and 4–7 may be provided for an optic 86 of a lens 88 in conjunction with an opposed haptic loop 90 having both its spaced ends rigidly secured to the optic 86 and extending outwardly from the peripheral edge of the optic 86. Noteworthy is the alignment of one leg of the haptic 90 with the inner stretch of the haptic 84 when the latter is in the position shown in FIG. 8.

Figure 9:
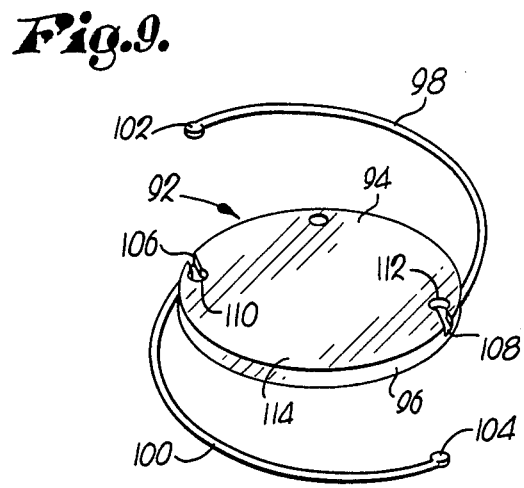
FIG. 9 is an elevational view of a fifth modified form of lens.

A lens 92 shown in FIG. 9 has an optic 94 provided with a peripheral edge 96 and a pair of haptics 90 and 100 extending from the edge 96 in the same manner as in FIG. 1, but the haptics 98, 100 have flat nodules 102 and 104 on their outer ends. Openings 106 and 108 in the optic 94 extend inwardly from the edge 96 and enlargements 110 and 112 are provided at the inner ends of the openings 106, 108. The openings 106, 108 and their enlargements 110, 112 extend through one face 114 of the optic 94. When the haptics 98, 100 are tensioned and releasably locked to the optic 94 the nodules 102, 104 are seated in the enlargements 110, 112 and portions of the haptics 98, 100 are received in the openings 106, 108.

Figure 10:
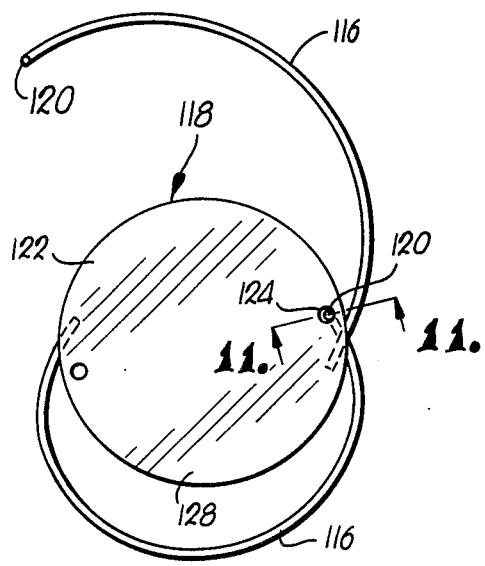
FIG. 10 is an elevational view of a sixth modified form of lens.
Figure 11:
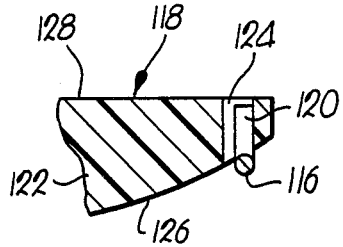
FIG. 11 is an enlarged, fragmentary, detailed, cross-sectional view taken on line 11—11 of FIG. 10.

In FIG. 10 and 11 of the drawings, haptics 116 for a lens 118 have right angle hooks 120, as distinguished from the hooks 26 and 28, and optic 122 has hook-receiving openings 124 which extend through the optic 122 from convex face 126 to planar face 128 thereof. The openings 124 may be the same as those illustrated at 20 in FIGS. 1, 2 and 7.

Figure 13:
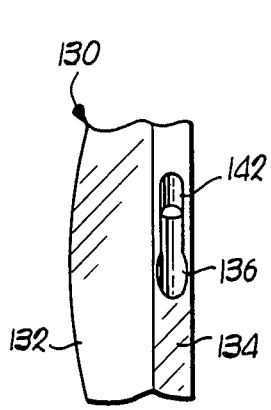
FIG. 13 is an edge view of the optic shown in FIG. 12 showing the haptic-receiving opening.
Figure 12:
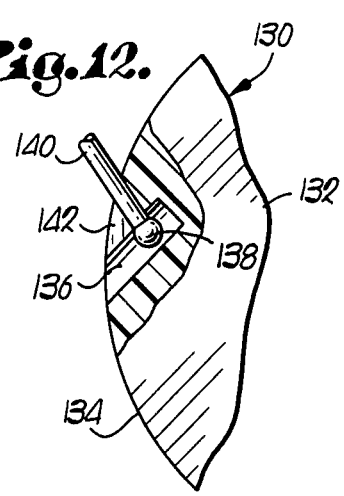
FIG. 12 is a fragmentary elevational view of a lens, partially in section, showing a modified form of releasable attachment of a haptic to the optic.
Figure 14:
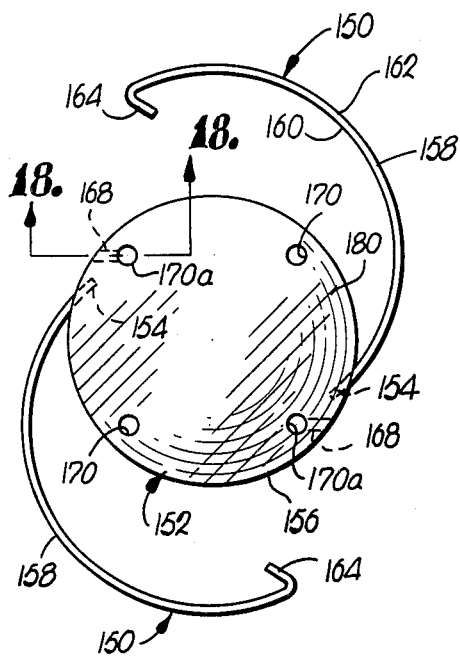
FIG. 14 is an elevational view of still another form of intraocular lens made in accordance with my present invention and adapted for use in my novel method of implantation thereof.
Figure 15:
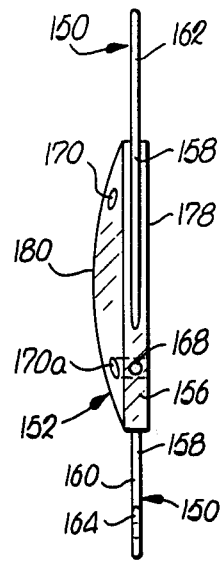
FIG. 15 is an edge view thereof.

In the embodiment of FIGS. 12 and 13 a lens 130 is provided with an optic 132 which includes a peripheral edge 134 having an opening in the nature of a keyhole slot. The opening has an enlarged outer portion 136 for receiving a spherical nodule 138 on a haptic 140 and an inner portion 142 of reduced size. The nodule 138 is inserted into the portion 136 and then moved into the portion 142 which holds the nodule 138 against displacement from the optic 132.

It is to be preferred that the lenses be packaged, shipped and stored with their haptics extended outwardly to avoid loss of memory and that they not be tensioned until immediately before implantation. The method of implantation of the several forms of lenses is much the same in each instance and need not be repeated.

In FIGS. 14–20 a pair of haptics 150 are oriented in relation to an optic 152 the same as the haptics 22 and 24 in FIG. 1, having their inner ends 154 diametrically opposed, extending into peripheral edge 156 of the optic 152 and affixed to the latter, with the haptics 150 extending obliquely from the edge 156 in the same direction circumferentially of the edge 156. Beyond the ends 154, each haptic 150 has a normally arcuate bight 158 with concavities 160 facing toward and convexities 162 facing away from the edge 156. If desired, each haptic 150 may, as shown, be a segment of a full circle. The overall length of each haptic 150 is greater than one half the circumferential length of the edge 156. Also, if desired, the edge 156 may be circular, as illustrated, and the haptics 150 are normally disposed eccentrically of the optic 152 as is clear in FIG. 14. The haptics 150 are preferably coplanar wtih their bights 158.

Figure 16:
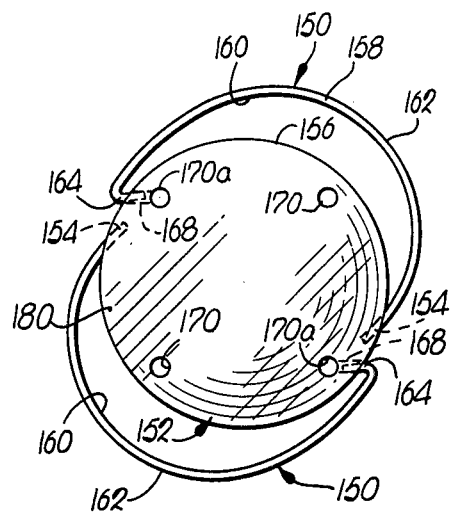
FIG. 16 is a view similar to FIG. 14 but showing the haptics in their releasably locked positions.
Figure 18:
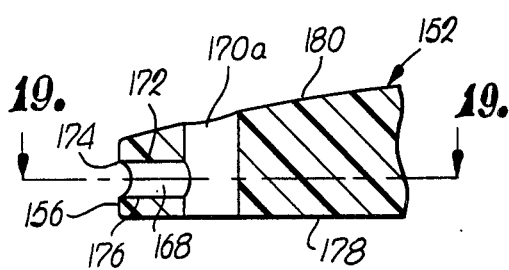
FIG. 18 is an enlarged fragmentary cross-sectional view through the optic of the lens illustrating one of the hook-receiving holes and its corresponding combination lens positioning and drainage hole.
Figure 17:
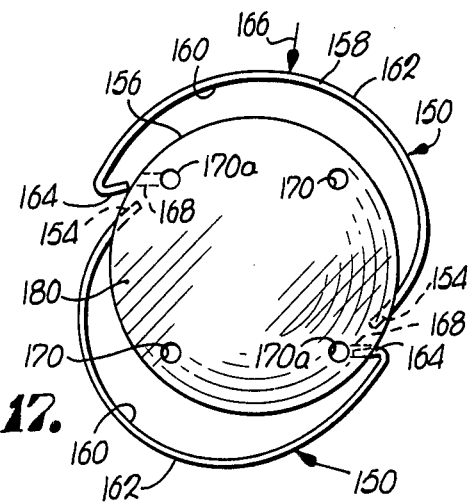
FIG. 17 is a view similar to FIG. 16 showing one of the haptics locked and illustrating the method of locking the other haptic which method may also be used for unlocking purposes.
Figure 19:
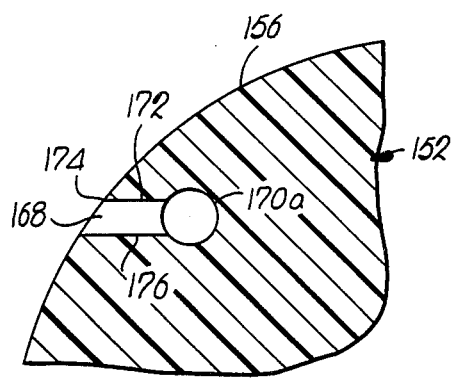
FIG. 19 is a fragmentary, cross-sectional view taken on line 19—19 of FIG. 18.

The outer end of each haptic 150 has a preformed hook 164, as in FIGS. 1, 4, 5 and 8, normally spaced radially outwardly from the edge 156, and each haptic 150 is, as above described in connection with FIGS. 1–13, made from resilient material such as to permit movement of the hooks 164 toward the edge 156 upon exertion of inward pressure on bights 158 of the haptics 150 as shown by arrow 166 in FIG. 16. Conversely the haptics 150 will spring back to their normal positions shown in FIG. 14 upon release of said pressure by virtue of the memory retaining properties of the haptics 150, all as previously described above.

As the hooks 164 approach a position adjacent or against the edge 156 (see FIG. 16) they may be easily manipulated to project into a corresponding hole 168 which extends into the optic 152 from the edge 156, the same as shown, for example, in FIG. 1. The same as hereinabove shown and described, each hole 168 is somewhat larger than its hook 164 in diameter such that the hooks 164 will easily and readily slip into and out of their holes 168. And, as hereinabove shown and described, the hooks 164 and their holes 168 have matched angularities. That is to say, there is an acute inner angle at each hook 164 and an angle for each hook-receiving hole 168 which is in a non-radial relationship to the edge 156. The haptics 150, and therefor, their hooks 160, as well as the holes 168, are preferably circular in transverse cross-section, as in the case of the modification of FIG. 1, for example.

Thus, all of the above is of extreme importance, first because of the fact that the hooks 164 are not formed by the holes 168 as they are inserted thereinto, retain their angularities on removal from the holes 168 and do not fit tightly in the holes 168 during and after insertion, thereby avoiding difficulty of insertion as would be the case of a tight or interference fit, and/or unmatched angularity. The hooks 164 are retained in the holes 168 by memory or tension, not by friction fit.

Figure 20:
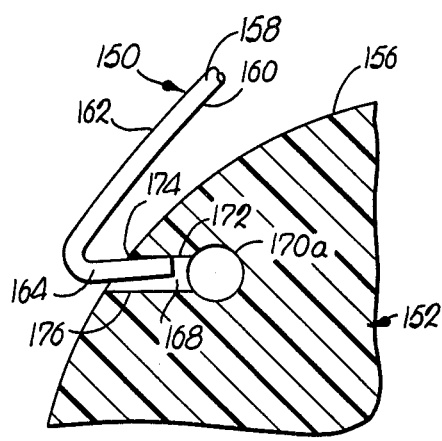
FIG. 20 is a fragmentary, cross-sectional view similar to FIG. 19 illustrating the way in which a corresponding hook of a haptic slides into and out of its locking hole.

Secondly, and perhaps even more importantly, the hooks 164 may be quickly and easily removed from the holes 168 after the lens is placed in the eye and properly positioned by use of lens-positioning holes 170 in the optic 152 perpendicular to face 178 of the latter. Such positioning is performed by use of a suitable tool (not shown) which is insertable into selected holes 170. During removal, as best shown in FIG. 20, as the bights 158 are depressed (see arrow 166, FIG. 17), the loosely fitted hooks 164 exit the holes 168 as soon as they clear walls 172 of the holes 168 and particularly corners 174 of the holes 168, all without interference by walls 76 of the holes 168. This is because of the fact that the diameters of the holes 168 are sufficiently large in relation of the diameters of the hooks 164 as to preclude the hooks 164 from dragging along the walls 176 during removal, as well as during insertion, unimpeded by substantial friction. The holes 170 extend entirely through the optics 152 whether the optic 152 has the flat face 178 and a convex face 180, as shown, or is provided with faces having other configurations. The prevention of binding of the hooks 164 in the holes 168 which would otherwise hinder release, is an important adjunct of my present invention.

The optics of the lens hereinabove disclosed are normally or oftentimes polished with substances toxic to the eye or interfere with vision. Thus, to provide holes 168 that are dead ended would trap the substances and release them into the eye. To avoid this problem, two of the holes 170a are disposed across the two corresponding locking holes 168 as shown, the holes 170a having, therefore, a second function. As shown, the holes 170a intersect the holes 168 at the inner ends of the latter and have larger diameters than the holes 168. But the holes 170a may have diameters which are either the same as or smaller than the diameters of the holes 168. But the combination positioning and drainage holes 170a need not be cylindrical in the manner illustrated by FIGS. 14–20. While the holes 170a are preferably provided in this manner, they need not necessarily drain from both of the faces 170 and 180 and might even be disposed to drain the substances from the holes 168 to the edge 156, obviating the function of use in positioning the optic 152 in the eye. Also, the holes 170a need not intersect the holes 168; instead, passages in the optic 156 (not shown) might be provided to interconnect the holes 168 and 170a.

It is preferred that the lengths of the holes 168 be less than the lengths of the hooks 168 such that, if the terminal ends of the hooks 168 should abut the inner ends of the holes 168, a portion of the hooks 168 will still protrude outwardly beyond the edge 156. This presents a space between the edge 156 and the curvature between hook 164 and its bight 158 capable of receiving a hook-like instrument used to remove the hook 164 from the hole 168 after the lens is in the eye.

I claim:

1. An intraocular lens adapted to be implanted in a human eye, said lens comprising:

an optic having a peripheral edge;

an elongated, resilient, memory retaining, position fixation haptic substantially within the plane of said edge, having an innermost end and a predetermined, normal, arcuate configuration;

means securing the haptic to the optic with the innermost end thereof extending into the optic through said edge, said haptic normally extending outwardly beyond the optic, terminating in an outermost, free end in spaced relationship to said edge, and being yieldable to a tensioned position prior to and during implantation of the lens in the eye, disposing its outermost end proximal to said edge, forming a loop presenting a bight spaced radially outwardly from said edge whereby, upon release of said tension after implantation, the haptic will return toward its normal configuration with its outermost end spaced from said edge; and releasable means for holding the haptic in its tensioned position, said releasable means being an attachment of the haptic to the optic, said attachment comprising an elongated, preformed hook at said free end substantially within the plane of the haptic, said optic having an elongated locking hole extending into said edge in chord-like relation to the optic and being larger than the hook for loosely receiving the hook.

2. The invention of claim 1, said hook being oriented at an angle relative to the adjacent portion of the haptic, the hook angle being selected for release of the haptic upon exertion of inward pressure on the loop at its bight toward said edge, ejecting the hook from its loose fit in the hole.

3. The invention of claim 1, said hole being angled toward the loop in a non-radial relationship to said optic, said hook having an angularity matching the angle of said hole.

4. An intraocular lens adapted to be implanted in a human eye, said lens comprising:

an optic having a peripheral edge;

an elongated, resilient, memory retaining, position fixation haptic having an innermost end and a predetermined, normal configuration;

means securing the haptic at the innermost end thereof to the optic adjacent said edge, said haptic normally extending outwardly beyond the optic, terminating in an outermost, free end in spaced relationship to said edge, and being yieldable to a tensioned position prior to and during implantation of the lens in the eye, disposing its outermost end proximal to said edge, forming a loop spaced radially outwardly from said edge whereby, upon release of said tension after implantation, the haptic will return toward its normal configuration with its outermost end spaced from said edge, releasable means for holding the haptic in its tensioned position, said releasable means being an attachment of the haptic to the optic, said attachment being preformed at said free end, said optic having a locking hole adapted to loosely receive the attachment; and means in the optic for draining substances tending to collect in said hole.

5. The invention of claim 4, said draining means being a hole in the optic communicating with the locking hole.

6. The invention of claim 5, said optic having a pair of opposed faces, said drainage hole extending through the optic face to face thereof.

7. The invention of claim 6, said locking hole having a closed innermost end, said drainage hole intersecting the locking hole at said innermost end.

8. The invention of claim 4, said optic having a lens-positioning hole, said draining means being the communication of said lens-positioning hole with said locking hole.

9. A method of implanting an intraocular lens in a human eye wherein the lens comprises an optic having a peripheral edge, an elongated, resilient, memory retaining, position fixation haptic having an innermost end and a predetermined, normal configuration, means securing the haptic at the innermost end thereof to the optic adjacent said edge, said haptic normally extending outwardly beyond the optic, terminating in an outermost, fee end in spaced relationship to said edge, said haptic having readily releasable means for attaching its free end to the optic, said method comprising the steps of:

tensioning the haptic inwardly toward the optic to form a loop adjacent said edge;

attaching the free end of the haptic to the optic to hold the haptic tensioned, said tensioned loop presenting a bight spaced from said edge;

inserting the lens into the eye while the haptic is tensioned; and detaching the free end of the haptic from the optic to release the tension thereon for return to its normal configuration with its outermost end spaced from said edge;

said detaching step comprising the step of exerting a force on the bight of said loop in a direction toward said edge for causing the free end of said haptic to be shifted away from said edge until said free end is released from the optic.

10. The invention of claim 9 wherein the optic has a pair of haptics, said method including the steps of tensioning both haptics, attaching the haptics to the optic to form a pair of loops, implanting the lens and detaching the haptics after implantation to release the tension on the haptics.

11. An intraocular lens adapted to be implanted in a human eye, said lens comprising:

an optic having a peripheral edge;

an elongated, resilient, memory retaining, position fixation haptic having an innermost end and a predetermined, normal configuration;

means securing the haptic at the innermost end thereof to the optic adjacent said edge, said haptic normally extending outwardly beyond the optic, terminating in an outermost, free end in spaced relationship to said edge, and being yieldable to a tensioned position prior to and during implantation of the lens in the eye, disposing its outermost end proximal to said edge, forming a loop spaced radially outwardly from said edge whereby, upon release of said tension after implantation, the haptic will return toward its normal configuration with its outermost end spaced from said edge; and releasable means for holding the haptic in its tensioned position, said releasable means being an attachment of the haptic to the optic, said attachment being preformed at said free end, said optic having a locking hole for receiving said attachment; and means in the optic for draining substances tending to collect in said hole.

12. The lens of claim 11, said draining means being a hole in the optic communicating with the locking hole.

13. The lens of claim 12, said optic having a pair of opposed faces, said drainage hole extending through the optic face to face thereof.

14. The lens of claim 13, said locking hole having a closed innermost end, said drainage hole intersecting the locking hole at said innermost end.

15. The lens of claims 11, said optic having a lens-positioning hole, said draining means being the communication of said lens-positioning hole with said locking hole.

* * * * *